United States Patent
Swaminathan et al.

(10) Patent No.: US 8,507,699 B2
(45) Date of Patent: Aug. 13, 2013

(54) BISPHENOL POLYMER STRUCTURAL UNITS AND METHOD OF MAKING THE SAME

(75) Inventors: Shubashree Swaminathan, Bangalore (IN); Venkata Ramanarayanan Ganapathy Bhotla, Bangalore (IN); Jean Francois Morizur, Evansville, IN (US)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 122 days.

(21) Appl. No.: 12/965,609

(22) Filed: Dec. 10, 2010

(65) Prior Publication Data

US 2012/0149923 A1 Jun. 14, 2012

(51) Int. Cl.
*C07D 493/04* (2006.01)
(52) U.S. Cl.
USPC .......................................................... 549/464

(58) Field of Classification Search
USPC .......................................................... 549/464
See application file for complete search history.

(56) References Cited

FOREIGN PATENT DOCUMENTS

| GB | 2330139 | 4/1999 |
|----|---------|--------|
| JP | 2004217600 | 8/2004 |
| WO | 2007120459 | 10/2007 |
| WO | 2009153168 | 12/2009 |

OTHER PUBLICATIONS

International Search Report for Application No. PCT/US2011/064203 dated Feb. 13, 2012 (3 pages).

*Primary Examiner* — Taofiq A Solola
(74) *Attorney, Agent, or Firm* — Michael Best & Friedrich LLP

(57) ABSTRACT

Provided herein are isosorbide-based bisphenol polymer structural units and methods of making the same. These structural units may be polymerized with one or more other types of structural units to form polymers, such as polycarbonates.

15 Claims, 2 Drawing Sheets

P-hydroxybenzoic acid

+

Isosorbide

Isosorbide-bisphenol

BISPHENOL POLYMER STRUCTURAL UNITS AND METHOD OF MAKING THE SAME

FIELD OF THE INVENTION

The present invention relates to the development and use of bisphenol-based polymer structural units.

BACKGROUND

Polymers based on aliphatic diols and in particular isosorbides are of great interest to the chemical industry. Isosorbides are derived from biologically based sources, namely sugars, rather than from the petroleum feed stocks used to prepare other structural units, or monomers. Isosorbide-based materials and products are biodegradable, have a low net environmental impact, and can be utilized as renewable resources by the plastic manufacturing industry. These materials and products can be used for the production of polymeric materials such as polycarbonates. Of particular interest are polymers based on isosorbides, such as 1,4:3,6-dianhydro-D-sorbitol; 2,6-dioxabicyclo[3.3.0]octan-4,8-diol; 1,4:3,6-dianhydro-D-glucitol; 2,3,3a,5,6a-hexahydrofuro[3,2-b]furan-3,6-diol, and isomers thereof.

Isosorbides are thermally unstable. As such, melt reactions conducted at above 220° C. can severely challenge the efficient production and commercial scale-up of isosorbide-based bisphenols via melt transesterification processes.

Accordingly, there is a need for efficiently producing isosorbide-based polymer structural units without sacrificing the commercial scale up capabilities of the production process. Such units can then be efficiently polymerized to form polymers that have desirable color properties (i.e. low yellowness) and acceptably high molecular weight for commercial application

SUMMARY OF THE INVENTION

The present invention is directed to a polymer structural unit that comprises an isosorbide unit and bisphenol. The polymer structural unit may have a pKa value of between 8 and 11. The polymer structural unit may comprise formula (I):

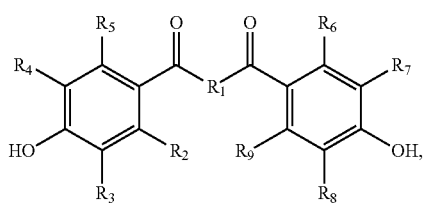

(I)

wherein R1 is an isosorbide unit and R2-R9 are independently selected from the group consisting of a hydrogen, a halogen, a C1-C6 alkyl, an arylalkyl, a methoxy, an ethoxy, an alkyl ester. Each structural unit may have a pKa value of between 8 and 11. R1 may be a derivative of any isosorbide. For example, R1 may be a derivative of 1,4:3,6-dianhydro-D-sorbitol; 2,6-dioxabicyclo[3.3.0]octan-4,8-diol; 1,4:3,6-dianhydro-D-glucitol; 2,3,3a,5,6a-hexahydrofuro[3,2-b]furan-3,6-diol, and/or isomers thereof.

The herein described polymer structural units may be made by a method that subjects a first reaction mixture of a first reactant, a second reactant, and a melt transesterification catalyst to melt transesterification conditions. The first reactant and second reactant may react to form the bisphenol structural unit. This reaction mixture may further comprise a solvent such as a hydrocarbon, xylene, hexane, benzene, cyclohexane, toluene, 1,2 dichloroethane, ethyl acetate, and mixtures thereof. The hydrocarbon may be, for example, ODCB (ortho-dichlorobenzene) or chlorobenzene. The first reactant, which is an isosorbide, may be melted and the second reactant may be added to, and mixed with, the melted isosorbide. A melt transesterification catalyst may be added to the melted isosorbide-second reactant mixture to form a first reaction mixture. The herein described steps may be performed in any order. The second reactant is

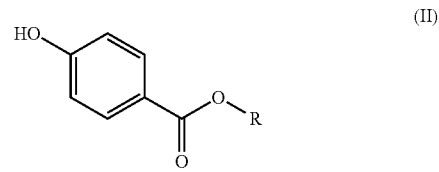

(II)

wherein R is selected from the group consisting of a hydrogen, a methyl, a C1-C6 alkyl, an arylalkyl, and an aromatic. The second reactant may be methyl-4-hydroxybenzoate.

The melt transesterification conditions include increasing the temperature of the first reaction mixture to between 180° C. and 250° C. The reaction mixture may then be cooled to between 60° C. and 120° C., and additional melt transesterification catalyst added to the cooled reaction mixture to form a second reaction mixture. In any of the foregoing reaction mixtures, the transesterification catalyst may be one or more of titanium isopropoxide, dibutyltin oxide, a hydroxide of an alkali metal, a hydroxide of an alkaline earth metal, an alkali metal salt, an alkaline earth metal salt, a quaternary ammonium salt of boron hydride, a quaternary ammonium salt of aluminum hydride, a hydride of an alkali metal, a hydride of an alkaline earth metal, an aryloxide of an alkali metal, an aryloxide of an alkaline earth metal, an organic salt of an alkali metal, an organic salt of an alkaline earth metal, a boron compound, a silicon compound, a germanium compound, a tin compound, an organotin compound, a lead compound, an onium compound, an antimony compound, a manganese compound, a titanium compound, and a zirconium compound. The melt transesterification catalyst may be the same or different between the first and second reaction mixtures.

DETAILED DESCRIPTION

Figure 1:
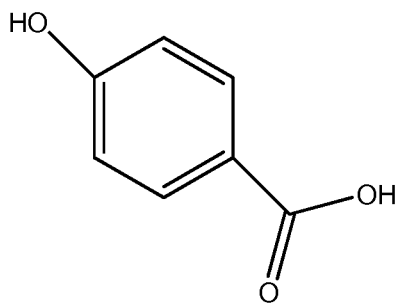
FIG. 1 shows an isosorbide-bisphenol synthetic scheme.
Figure 1:
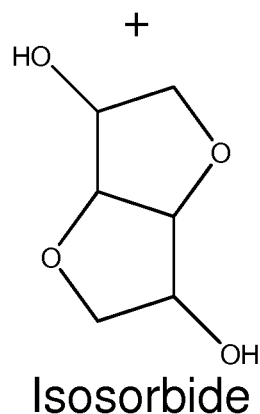
Figure 1:
Figure 1:
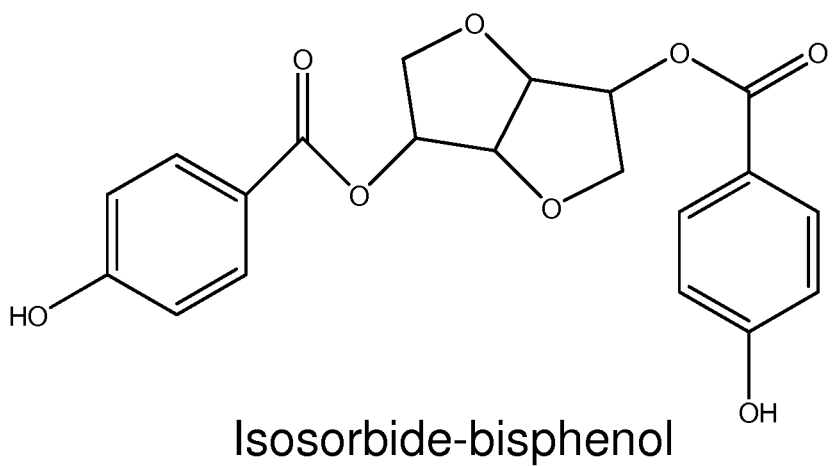

Use of the herein described bisphenols as polymer structural units allows for the efficient production of polymers capable for use in a variety of applications where, for example, low color, excellent toughness and UV stability are needed. The inventor has discovered that melt transesterification may be used to produce isosorbide-based bisphenols, which can be utilized in processes for making polymers. In general, specific melt transesterification components are reacted to produce an isosorbide-based bisphenol product.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

"Alkyl" as used herein may be linear, branched, or cyclic such as a methyl group, ethyl group, n-propyl group, isopropyl group, n-butyl group, isobutyl group, tert-butyl group, n-pentyl group, isopentyl group, n-hexyl group, isohexyl group, cyclopentyl group, cyclohexyl group, and the like.

"C3-C6 cycloalkyl" as used herein may mean cyclopropyl, cyclobutyl, cyclopentyl and cyclohexyl.

"Halogen" or "halogen atom" as used herein may mean a fluorine, chlorine, bromine or iodine atom.

"Heteroaryl" as used herein may mean any aromatic heterocyclic ring which may comprise an optionally benzocondensed 5 or 6 membered heterocycle with from 1 to 3 heteroatoms selected among N, O or S, Non limiting examples of heteroaryl groups may include pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazotyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, and the like.

"$pK_a$" as used herein may mean the $-\log_{in}$ of $K_a$, where $K_a$ is a value used to describe the tendency of compounds or ions to dissociate. The $K_a$ value may be referred to as "the dissociation constant," "the ionization constant," or "the acid constant." Phenolic compounds may have a $pK_a$ of between 8 and 11.

"Polycarbonate" as used herein may mean an oligomer or polymer comprising residues of one or more polymer structural units, or monomers, joined by carbonate linkages.

"Straight or branched C1-C3 alkyl" or "straight or branched C1-C3 alkoxy" as used herein may mean methyl, ethyl, n-propyl, isopropyl, methoxy, ethoxy, n-propoxy and isopropoxy.

Unless otherwise indicated, each of the foregoing groups may be unsubstituted or substituted, provided that the substitution does not significantly adversely affect synthesis, stability, or use of the compound.

"Substituted" as used herein may mean that any at least one hydrogen on the designated atom or group is replaced with another group provided that the designated atom's normal valence is not exceeded. For example, when the substituent is oxo (i.e., =O), then two hydrogens on the atom are replaced. Combinations of substituents and/or variables are permissible provided that the substitutions do not significantly adversely affect synthesis or use of the compound.

The terms "structural unit" and "monomer" are interchangeable as used herein.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Melt Transesterification Components

An isosorbide-based bisphenol is produced by reacting specific components under melt transesterification conditions. Specifically, an isosorbide-based bisphenol is produced when an isosorbide first reactant is mixed with a second reactant in the presence of a catalyst and, optionally, a solvent under melt-transesterification conditions.

a. First Reactant

Described herein is a monomer formed from, in part, a first reactant. The first reactant may provide for increased efficiency of bisphenol production. The first reactant may be a diol, such as an aliphatic diol. The aliphatic diol may have improved solubility and/or reactivity in the solvent as compared to other reactants. The improved solubility and/or reactivity may be attributable to the presence of hydroxyl groups of the aliphatic diol. The aliphatic diol may be an isosorbide unit. The isosorbide unit may be derived from an isosorbide. For example, the isosorbide unit may be a derivative of one or more of 1,4:3,6-dianhydro-D-sorbitol; 2,6-dioxabicyclo[3.3.0]octan-4,8-diol; 1,4:3,6-dianhydro-D-glucitol; 2,3,3a,5,6a-hexahydrofuro[3,2-b]furan-3,6-diol, and/or an isomer thereof.

The isosorbide unit may be derived from an isosorbide, a mixture of isosorbide, a mixture of isomers of isosorbide, and/or from individual isomers of isosorbide. The stereochemistry for the isosorbide-based carbonate units of formula III is not particularly limited. Specifically, isosorbide has the general formula III:

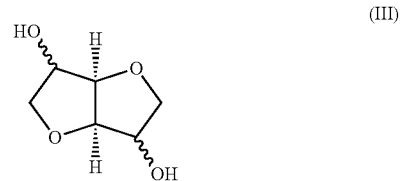

(III)

and can be a single diol isomer or mixture of diol isomers. The stereochemistry for the isosorbide of formula III is also not particularly limited. These diols may be prepared by the dehydration of the corresponding hexitols. Hexitols are produced commercially from the corresponding sugars (aldohexose). Aliphatic diols of formula III include 1,4:3,6-dianhydro-D glucitol, of formula IV; 1,4:3,6-dianhydro-D mannitol, of formula V; and 1,4:3,6-dianhydro-L iditol, of formula VI, and any combination thereof. Isosorbides are available commercially from various chemical suppliers including Archer Daniels Midland Company, Cargill, Roquette, and Shanxi.

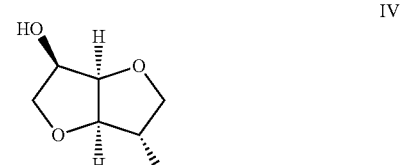

IV

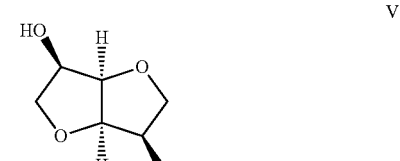

V

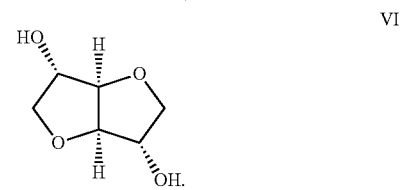

VI

The diol of formula IV may be desirable because it is rigid, chemically and thermally stable aliphatic diol that may be used to produce higher Tg copolymers than the other diols of formulas V and VI.

The isosorbide may have moisture content of less than 5%.
The isosorbide may have a pKa value of greater than 12.
The isosorbide may be made from a biomass derived starch through hydrolysis, hydrogenation, and dehydration reactions. For example,

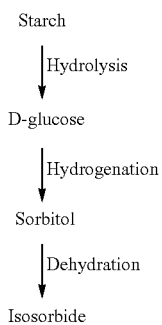

Isosorbide provided by many commercial suppliers may contain sorbitol, which may be present due to the incomplete conversion to isosorbide. Sorbitol may react to form sorbitol-derived color bodies at elevated temperatures and extended reaction times of various reaction mixtures. The isosorbide may be tested for the presence of sorbitol and treated to reduce the concentration of sorbitol prior to polymerization. The isosorbide may be treated to reduce the concentration of sorbitol regardless of whether it is present or not. The sorbitol content in isosorbide may be measured by an organic purity measurement method such as chromatography. Such chromatographic methods include gas chromatography, and high performance liquid chromatography.

b. Second Reactant

The second reactant reacts with the first reactant under appropriate conditions to form the bisphenol polymer structural unit. The second reactant may have the following formula:

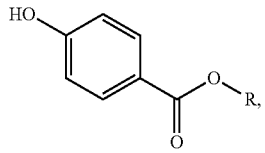

wherein R is selected from the group consisting of a hydrogen, a C1-C6 alkyl, and an aromatic compound. The aromatic compound may be a substituted aromatic, such as a phenol. The phenol may be substituted. The aromatic compound may be substituted with a hydroxyl, alkoxy, alkoxycarbonyl, arylalkyl, halogen, sulfide, sulfate, nitrate, amino, nitrile, and/or nitro group. The aromatic compound may contain alkyl substituents of one or more carbon atoms per alkyl substituent. The aromatic compounds may be mono-nuclear or polynuclear and may contain one or more alkyl substituents. For example, the second reactant may be a mono-, di-, tri-, or tetra-alkyl substituted aromatic hydrocarbon, such as a dimethylbenzene, trimethylbenzene, dimethylnaphthalene, trimethylnaphthalene, tetramethylnaphthalene, diethylbenzene, mono-methylbenzene, monoethylbenzene, monomethylnaphthalene, diethylnaphthalene, methylphenanthrene, dimethyl anthracene, dimethylpyrene, tetraethyl phenanthrene, dimethylchrysene, tetraethyl pyrene, trimethyl anthracene, diethyl-dimethyl phenanthrene, methyl ethylbenzene, methyl ethyl naphthalene, and the like. The alkyl substituent may have 2 or more carbon atoms. The aromatic compound may be heterocyclic.

The second reactant may have a pKa value such that, when the second reactant reacts with the first reactant, a bisphenol is produced that has a pKa value of between 8 and 11. The second reactant may be methyl-4-hydroxybenzoate.

c. Catalyst

The melt transesterification catalyst may be one or more of titanium isopropoxide, a hydroxide of an alkali metal, a hydroxide of an alkaline earth metal, an alkali metal salt, an alkaline earth metal salt, a quaternary ammonium salt of boron hydride, a quaternary ammonium salt of aluminum hydride, a hydride of an alkali metal, a hydride of an alkaline earth metal, an aryloxide of an alkali metal, an aryloxide of an alkaline earth metal, an organic salt of an alkali metal, an organic salt of an alkaline earth metal, a boron compound, a silicon compound, a germanium compound, a tin compound, an organotin compound, a lead compound, an onium compound, an antimony compound, a manganese compound, a titanium compound, and a zirconium compound.

The hydroxide of an alkali metal or an alkaline earth metal may be a lithium hydroxide, a sodium hydroxide, a potassium hydroxide or a calcium hydroxide. The quaternary ammonium salts of boron hydride and of aluminum hydride may be a lithium aluminum hydride, sodium boron hydride and tetramethyl ammonium boron hydride. The hydrides of an alkali metal and of an alkaline earth metal may be lithium hydride, sodium hydride or calcium hydride. The alkoxides of an alkali metal and of an alkaline earth metal may be lithium methoxide, sodium ethoxide or calcium methoxide. The aryloxides of an alkali metal and of an alkaline earth metal may be lithium phenoxide, sodium phenoxide, magnesium phenoxide, LiO—Ar—OLi, wherein Ar represents an arylene group, and NaO—Ar—ONa, wherein Ar is an arylene group. The organic salts of an alkali metal and of an alkaline earth metal may be lithium acetate, calcium acetate or sodium benzoate. The zinc compounds may be zinc oxide, zinc acetate or zinc phenoxide. The boron compounds may be boron oxide, boric acid, sodium borate, trimethyl borate, tributyl borate, triphenyl borate, ammonium borate or phosphonium borate. The silicon compounds may be silicon oxide, sodium silicate, tetraalkylsilicon, tetraarylsilicon or diphenyl-ethyl-ethoxy-silicon. The germanium compounds may be germanium oxide, germanium tetrachloride, germanium ethoxide or germanium phenoxide. The tin compounds may be tin oxide, dialkyltin oxide, dibutyltin oxide, dialkyltin carboxylate or tin acetate. The tin compounds that have an alkoxy group or an aryloxy group bonded to tin may include ethyltin tributoxide and organotin compounds. Lead compounds include lead oxide, lead acetate, lead carbonate and basic lead carbonate. Alkoxides and aryloxides of lead or organolead may also be used as a metal transesterification catalyst. Onium compounds may include quaternary ammonium salt, quaternary phosphonium salt, or a quaternary arsonium salt. The antimony compounds may include antimony oxide and antimony acetate. The manganese compounds may include manganese acetate, manganese carbonate and manganese borate. The titanium compounds include titanium oxide and titanium alkoxides and titanium aryloxide. The zirconium compounds include zirconium acetate, zierconium oxide, circonium alkoxide, zirconium aryloxide, and zirconium acetylacetonate.

In addition to the foregoing, transesterification catalysts used herein may include tetrabutylammonium hydroxide, methyltributylammonium hydroxide, tetrabutylammonium acetate, tetrabutylphosphonium hydroxide, tetrabutylphosphonium acetate, and/or tetrabutylphosphonium phenolate.

The transesterification catalyst as used herein may be one or more of the foregoing compounds.

d. Solvent

A solvent may be used as a reagent during melt transesterification. The solvent may be added at any step before, after, or during the melt transesterification. The solvent may drive the transesterification at temperatures optimal for efficient and high conversion to the bisphenol product.

The solvent may be any solvent. The solvent may be an organic solvent. The solvent may be aromatic. The solvent may be a hydrocarbon, xylene, hexane, benzene, cyclohexane, toluene, 1,2-dichloroethane, and/or ethyl acetate. The hydrocarbon may be, for example, ODCB or chlorobenzene. The solvent may be a polar solvent. The polar solvent may be acetonitrile, methanol, ethanol, isopropanol, 1,4-dioxane, dimethylformamide, dimethyl sulphoxide, and/or dialkyl ether. The solvent may be a hydrocarbon. The hydrocarbon may be chloroform, dichloromethane, dichloroethane, chloroalkane, dichlorobenzene, ortho-dichlorobenzene, (ODCB), toluene, xylene, benzene, etc. The solvent may be a mixture of two or more solvents. The mixture may be ethyl acetate:hexane. The mixture may be a 50:50 (1 wt/1 vol.) mixture. The organic solvent may have at least 1 carbon atom and 1 hydrogen atom, have a low molecular weight, and exist in liquid form at room temperature. The solvent may be an aliphatic-chain compound, such as n-hexane. The solvent may be an aromatic compound with a 6-carbon ring, such as benzene or xylene. The aliphatic or aromatic solvent may contain a substituted halogen element and may be referred to as a halogenated hydrocarbon, such as perchloroethylene (PCE or PER), trichloroethylene (TCE), and carbon tetrachloride. Alcohols, ketones, glycols, esters, ethers, aldehydes, and pyridines may be substitutions for a hydrogen group.

The solvent may allow for the first reactant and the second reactant to react at temperatures lower than 250° C., thereby avoiding any significant degradation of the first reactant. In the presence of the solvent, the first and second reactants may react at 230° C., between 175° C. and 220° C. or between 180° C. and 200° C. without significant degradation of the first reactant, especially isosorbide.

3. Method of Making Bisphenol

The method of making isosorbide-based bisphenol centers on subjecting a mixture of transesterification components ("first reaction mixture") to melt transesterification conditions to produce the bisphenol. Optionally, the final yield of bisphenol may be increased via the manufacture of a second reaction mixture that is also subjected to melt transesterification conditions.

a. Melt Transesterification Conditions—Generally

The bisphenol may be made under melt transesterification conditions. Generally, in melt esterification, temperature conditions and the presence of the transesterification catalyst and, optionally, a specific solvent, drive the formation of the bisphenol. See FIG. 1, for example. More specifically, the bisphenol may be prepared by reacting molten first reactant with the second reactant in the presence of a transesterification catalyst. The first reactant, second reactant, and transesterification catalyst may be combined in any order in a mixer or extruder to form a dispersion or slurry. The dispersion may then be cooled whereby it is refluxed with a solvent to precipitate the desired bisphenol.

b. Forming the First Reaction Mixture

The molten state condition may be produced by increasing the temperature of the first reactant with or without a solvent. The temperature may be between 70° C. and 200° C., between 90° C. and 165° C., between 115° C. and 160° C., or between 120° C. and 150° C. so as to melt the first reactant. This temperature may be maintained for between 0 and 30 minutes, between 5 and 25 minutes, between 10 and 20 minutes, or between 10 and 15 minutes, after which the second reactant is mixed into the melted first reactant to form a slurry. The slurry may be uniform. The transesterification catalyst may then be added to the slurry to form the first reaction mixture.

(1) Melt Transesterification and the First Reaction Mixture

Generally, the transesterification catalyst catalyzes the formation of bisphenol in the first reaction mixture. The formed bisphenol may be isolated and further purified from the first reaction mixture.

Subjecting the first reaction mixture to melt transesterification conditions involves increasing the temperature of the first reaction mixture to between 150° C. and 250° C. The temperature of the first reaction mixture may be increased to between 180° C. and 250° C. The temperature of the first reaction mixture may be increased to 160° C., 170° C., 180° C., 190° C., 200° C., 210° C., 220° C., 225° C., 230° C., 235° C., 240° C., 245° C., or 250° C. If a solvent is a component in the first reaction mixture, the increased temperature of the first reaction mixture may be between 150° C. and 190° C., between 155° C. and 185° C., between 160° C. and 180° C., or between 165° C. and 175° C. Temperatures lower than 220° C., 230° C., or 240° C. may result in increased stability of the first reactant. This temperature may be maintained for greater than 8 hours. This temperature may be maintained for between 8 and 24 hours, between 10 and 20 hours, or between 12 and 18 hours. The temperature may be maintained for 12 hours or 18 hours. The solvent and/or any methanol that is formed may be distilled off. The methanol and/or other solvent may be distilled off continuously or collected at one or more points during or after the increased temperature maintenance period.

After the increased temperature maintenance period, the temperature may be cooled to between 90° C. and 140° C., 60° C. and 120° C., 70° C. and 130° C., 80° C. and 125° C., between 95° C. and 135° C., between 100° C. and 130° C., between 105° C. and 125° C., between 110° C. and 120° C., or between 110° C. and 115° C. The temperature may be cooled to 100° C. or 120° C. The progress of the reaction may be monitored by HPLC for selectivity of the required product, which may be >60%, >70%, >80%, >90%, >95%, or >98% of the reaction mixture.

Solvent may be added to the cooled reaction mixture and the mixture refluxed for a period of time to precipitate the bisphenol. The mixture may be refluxed for between 2 and 8 hours, between 3 and 6 hours, or between 4 and 5 hours. The mixture may be refluxed for 3 hours. The mixture may be cooled to room temperature (~25° C.) to complete precipitation of the bisphenol product. The mixture may stand at room temperature for between 1 and 10 hours, between 2 and 8 hours, between 3 and 6 hours, or between 4 and 5 hours. The mixture may stand at room temperature for 4 hours. The product precipitate may be filtered and washed with solvent. The washed bisphenol product precipitate may then be dried. The first reaction mixture may yield between 10% and 90% bisphenol product. The bisphenol product may be purified. The purification may result in a yield of between 1% and 99%, between 10% and 95%, between 20% and 90%, or between 30% and 85% bisphenol product.

Example 1, provided below, demonstrates the efficiency of isosorbide-bisphenol production and the high conversion rate of a first reaction mixture that is subjected to transesterification conditions.

c. Second Reaction Mixture

After the temperature of the first reaction mixture is cooled from the increased temperature maintenance period, and instead of adding solvent to the cooled reaction mixture to precipitate the bisphenol, additional transesterification catalyst may be added to the mixture to form a second reaction mixture. The second reaction mixture may be formed to increase the final yield of bisphenol product. The additional transesterification catalyst may replace sublimed catalyst used in the first reaction mixture.

The components of the second reaction mixture may be mixed to form a dispersion or slurry. The second reaction mixture may also comprise the solvent as an additional component. The components may be mixed in a mixer or an extruder. The temperature of the second reaction mixture may be increased to between 220° C. and 230° C. The temperature of the second reaction mixture may be 220° C., 225° C., or 230° C. This temperature may be maintained for greater than 8 hours. This temperature may be maintained for between 8 and 24 hours, between 10 and 20 hours, or between 12 and 18 hours. The temperature may be maintained for 10 hours, 12 hours or 18 hours. Any methanol that is formed may be distilled off. The methanol may be distilled off continuously or collected at one or more points during or after the increased temperature maintenance period. Reaction progress may be monitored via HPLC.

After the increased temperature maintenance period, the temperature may be cooled to between 90° C. and 140° C., between 95° C. and 135° C., between 100° C. and 130° C., 105° C. and 125° C., or between 110° C. and 120° C. The temperature may be cooled to 100° C. or 120° C.

The first solvent may be added to the cooled second reaction mixture and the mixture refluxed for a period of time to precipitate the bisphenol. The mixture may be refluxed for between 0.5 and 5 hours, between 1 and 4 hours, or between 2 and 3 hours. The mixture may be refluxed for 1 hour. Any solid waste generated by the reaction may be filtered and the filtrate evaporated to obtain solid material. A second solvent, which may or may not be the same as the first solvent, may be added to the solid material and the solvent-solid material mixture refluxed for between 1 and 5 hours, or between 2 and 4 hours. The solvent-solid material mixture may be refluxed for 3 hours. The material may then be cooled to room temperature (~25° C.) to complete precipitation. The precipitated solid bisphenol product may be filtered and washed with solvent. The solvent may be warmed to between 50° C. and 200° C., between 60° C. and 190° C., between 70° C. and 180° C., between 80° C. and 170° C., between 90° C. and 160° C., between 100° C. and 150° C., between 110° C. and 140° C., between 115° C. and 135° C., or between 120° C. and 130° C. prior to washing the product. The washed bisphenol product may then be dried.

(1) Mixers and Extruders

The mixer may be any mixer. Several mixers are commercially available and may be used in conjunction with the above-described methods. Examples of mixers may be found in U.S. Pat. Nos. 4,419,014 and 7,097,345, which are herein incorporated by reference in their entirety. The mixer may be any mixer that is generally used for mixing one or more raw materials. The mixer may be a continuous mixer or a batch mixer. The continuous mixer may be a kneader mixer or a pug mixer. The mixer may adjust the temperature of the raw material.

4. Bisphenol

Provided herein is a bisphenol polymer structural unit for making polymers. The bisphenol may be represented by formula (I):

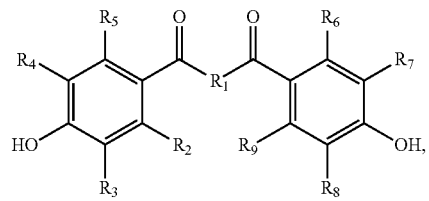

wherein R1 is an isosorbide and R2-R9 may be independently selected from the group consisting of a hydrogen, a halogen, a C1-C6 alkyl, a methoxy, an ethoxy, an alkyl ester and an arylalkyl. The bisphenol may have a pKa of between 8 and 11.

a. Alkali Metals

Alkali metals, such as lithium, sodium, and potassium, are known to be impurities in several monomer compounds and especially in dihydroxy compounds. They can be present individually or combined as salts or as some other structures with other chemicals. Alkali metals can act as a catalyst to the polymerization reaction. To reduce the tendency of the reaction mixture to react, a monomer conditioning step of testing and treating, or simply treating the monomer compound, to reduce alkali metal to a level of less then 600 ppb, or adding an acid stabilizer to the monomer, or a combination of the two treatment steps. It is believed that when the alkali metal has a presence of less than 600 ppb, less than 400 ppb, less then 200 ppb, or where an acid stabilizer is present that its catalytic effect can be minimized. Where the monomer component is tested for the presence of the alkali metal, the testing mechanism is not particularly limited and can be accomplished by known methods of determining concentration of the alkali metal. The step of testing may be performed at the structural units' production facility, a certification agency, a laboratory, or warehouse, for example. The bisphenol structural units may be assigned an alkali metal grading value.

It is believed that the addition of the acid stabilizer also aids in hindering the catalytic effect of the alkali metal and hence in delaying the transesterification reaction to form a polymer, such as a polycarbonate oligomers and polymers. The acid stabilizer may be added to the structural units by itself or when the structural units are combined with other reactants. Where the acid stabilizer is added, the addition mechanism may be accomplished by known methods of adding additives.

Suitable acid stabilizers include acids, acid salts, esters of acids or their combinations. The addition of the acid or its salt or ester often deactivates catalytically active species such as alkali metals. Particularly useful classes of acids, acid salts and esters of acids are those derived from a phosphorous containing acid such as phosphoric acid, phosphorous acid, hypophosphorous acid, hypophosphoric acid, phosphinic acid, phosphonic acid, metaphosphoric acid, hexametaphosphoric acid, thiophosphoric acid, fluorophosphoric acid, difluorophosphoric acid, fluorophosphorous acid, difluorophosphorous acid, fluorohypophosphorous acid, fluorohypophosphoric acid, or their combinations.

5. Subsequent Use of Bisphenol Polymer Structural Units

The bisphenol polymer structural units may be used in the formation of a polymer, such as a polycarbonate. The structural units may be subjected to melt polymerization or interfacial polymerization by adding a catalyst and allowing the mixture to react under melt or interfacial conditions. The structural units may be polymerized with one or more other types of structural units, or monomers.

The present invention can be utilized as illustrated by the following non-limiting example.

EXAMPLE 1

Isosorbide Ester Bisphenol Via Transesterification 50.0 g (0.342 mol) of isosorbide was taken in a 2-necked R.B. fitted with a nitrogen inlet and a Dean & Stark. The moisture content of isosorbide should be <5 wt %. A slow nitrogen flow should be maintained to avoid the sublimation of methyl-4-hydroxybenzoate. To this 50 ml of xylene was added. The bath temperature was slowly increased to 150° C. (0.986 mol.) of methyl-4-hydroxybenzoate was added. The reaction mixture was thoroughly mixed to form a slurry and the bath temperature was gradually increased to 180° C. during which, 3.5 g (0.00986 mol.) of dibutyltin oxide was added. The reaction mixture was kept with stirring at that temperature for 18 hours. The reaction mixture forms a clear solution. Excess xylene and methanol, which is formed during the reaction, was collected in the Dean & Stark apparatus. About 60 ml of the methanol and xylene was collected at the end of the reaction. Most of the xylene and moisture is distilled away in the first 3 to 4 hours. At the end of 18 hours, the selectivity (area %) of mono v/s diester (desired product) formed was monitored using HPLC. Relative area % is measured. Major peaks formed during this reaction as seen from HPLC are monoester (mixture of 2 isomers)=10.93%, methyl-4-hydroxybenzoate (not integrated as it is taken in excess), product diester monomer at 80%, and oligomers at 7%. The reaction mixture was then cooled to 100° C. (internal temperature) following which 150 ml of 1,2-dichloroethane was added and the mixture was refluxed for 3 hours when the desired product precipitates out. The reaction mixture was then cooled to room temperature and made to stand for 4 hours at room temperature for complete precipitation of the desired product. The precipitated solid was filtered, washed thoroughly with boiling dichloroethane (~200 ml) and dried. 75.0 g (yield ~57%) of off-white solid with purity 97% was obtained. The crude material obtained was further purified by crystallization.

50.0 g of the crude material was refluxed (to dissolve) in 600 ml of EtOAc. To this 5.0 g of activated charcoal was added and the mixture was heated to reflux for 1 h. The charcoal was filtered and washed thoroughly with boiling EtOAc (150 ml). The volume of the filtrate obtained was reduced in a rotary evaporator under vacuum to 2 wt/vol. (i.e. 100 ml) when the desired product monomer begins to crystallize. The mixture was allowed to stand at room temperature for about 5 hours. Complete crystallization of the desired product is ensured by cooling the material (to 0° C.) in ice for 2 hours. Precipitated solid is filtered, washed with ice cold EtOAc:Hexane (50:50/1 wt/vol.) solvent mixture and dried. 40.0 g of the pure isosorbide ester (off-white) with purity 99.4% was obtained.

Characterization of the product: M.P.=188.3° C. and 202.97° C. $^1$H NMR (DMSO-$d_6$, 300 MHz): δ 10.4 (s, 2H, Ar—OH), δ 7.8 (d, 4H, Ar—H), δ 6.8 (d, 4H, Ar—H), δ 5.4-5.2 (m, 2H, H—OCO), δ 4.8-4.6 (2d, 2H, H—CO—), δ 4-3.8 (m, 4H, —$CH_2$). LC/MS: 387.8 (M+1). See FIG. 3.

EXAMPLE 2

Melt Process for Making Isosorbide-Based Bisphenol 50.0 g (0.0342 mol.) of isosorbide was taken in a two-necked round bottom flask fitted with a nitrogen inlet and distillation condenser. The bath temperature was slowly increased to 120° C. during which the isosorbide melts and was maintained at that temperature for 10-15 minutes. To this was added 150.0 g (0.986 mol.) of methyl-4-hydroxybenzoate at the same temperature. The reaction mixture was thoroughly mixed to form a uniform slurry. Then 1.0 g (0.0035 mol.) of titanium isopropoxide was added and the bath temperature was raised to 220° C. The reaction mixture was maintained at this temperature for 12 hours. Methanol formed during the reaction was distilled off continuously. After completion of 12 hours, the reaction mixture was cooled to 120° C. and another 0.5 g (0.0017 mol.) of titanium isopropoxide was added. The bath temperature was increased to 220° C. and the reaction mixture was maintained at that temperature for another 10 hours. Reaction progress was monitored by HPLC. The reaction mixture was then cooled to 110° C. (bath temperature), following which 500 ml of ethyl acetate was added. The mixture was refluxed for 1 hour and filtered (to remove any solid waste generated by catalyst). The filtrate was evaporated under vacuum to obtain a dark brown sticky material. To this 400 ml of 1,2-dichloroethane was added and the mixture was refluxed for 3 hours and then cooled to room temperature and the precipitated solid was filtered, washed thoroughly with hot dichloroethane and dried, 35.0 g (yield ~30%) of brownish yellow solid with purity 90% was obtained. This was further purified by crystallization using ethylacetate as solvent.

Figure 2:
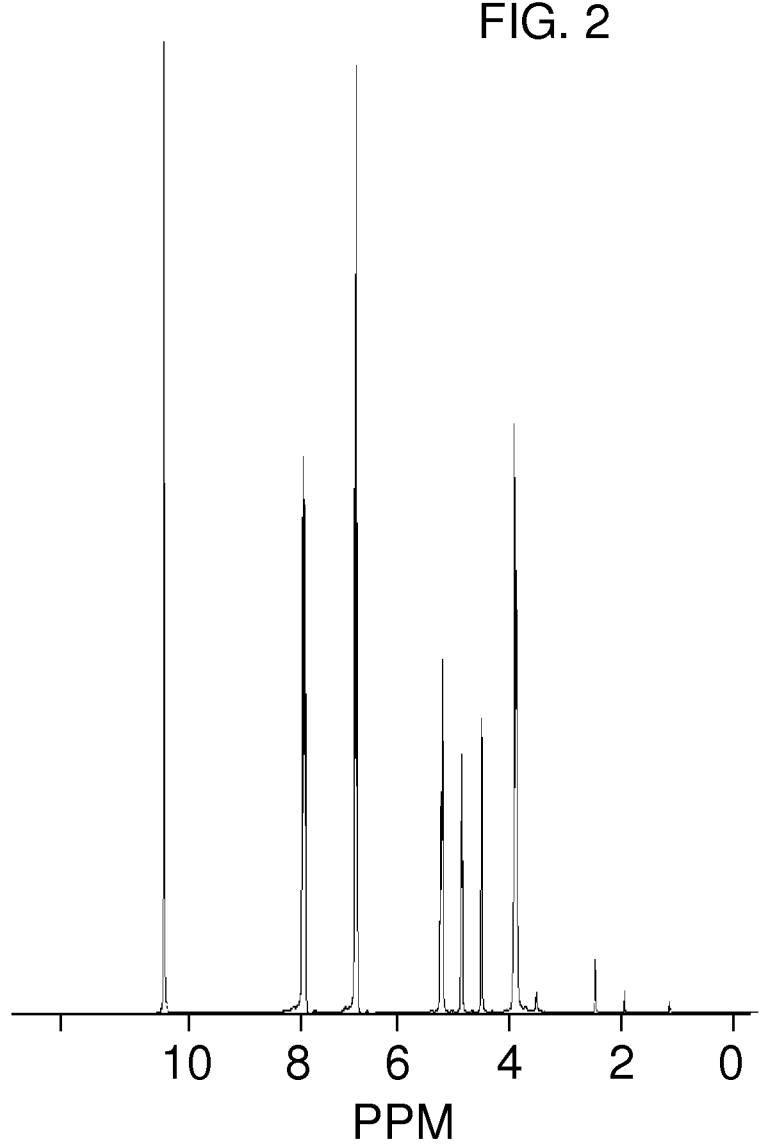
FIG. 2 shows $^1$H NMR spectrum of isosorbide-2,5-bis(4-hydroxybenzoate).

Representative NMR chemical shifts: H1 NMR (DMSO-$d_6$, 300 MHz): δ 10.4 (s, 2H, Ar—OH), δ 7.8 (d, 4H, Ar—H), δ 6.8 (d, 4H, Ar—H), δ 5.4-5.2 (m, 2H, H—OCO), δ 4.8-4.6 (2d, 2H, H—CO—), δ 4-3.8 (m, 4H, —$CH_2$). See FIG. 2.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

We claim:

1. A bisphenol for use as a polymer structural unit comprising formula (I):

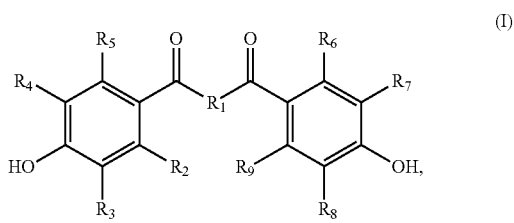

wherein R1 is an isosorbide unit and R2-R9 are independently selected from the group consisting of a halogen, an arylalkyl, an ethoxy, and an alkyl ester.

2. A method of making a bisphenol for use as a polymer structural unit, wherein the bisphenol comprises formula (I):

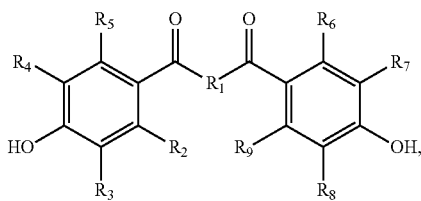

wherein R1 is an isosorbide unit and R2-R9 are independently selected from the group consisting of a hydrogen, a halogen, an arylalkyl, a C1-C6 alkyl, and an alkyl ester, comprising subjecting a first reaction mixture of a first reactant, a second reactant, and a melt transesterification catalyst to melt transesterification conditions, wherein the first reactant is an isosorbide and the second reactant is

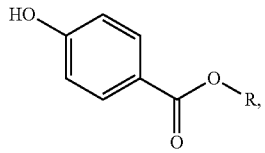

wherein R is selected from the group consisting of a hydrogen, a methyl, a C1-C6 alkyl, and an aromatic, and wherein the second reactant reacts with the isosorbide to form the bisphenol of formula (I).

3. The method of claim 2, wherein the first reaction mixture is formed by the following steps, in any order:
(a) melting an isosorbide reactant;
(b) adding and mixing a second reactant to the melted isosorbide reactant; and
(c) adding a melt transesterification catalyst to (b) to form the reaction mixture.

4. The method of claim 3, wherein the reaction mixture further comprises a solvent.

5. The method of claim 4, wherein the solvent is selected from the group consisting of a hydrocarbon, xylene, hexane, benzene, cyclohexane, toluene, 1,2-dichloroethane, ethyl acetate, ortho-dichlorobenzene, chlorobenzene, and a mixture thereof.

6. The method of claim 2, wherein R is a methyl.

7. The method of claim 2, wherein R is a hydrogen.

8. The method of claim 2, wherein the melt transesterification conditions comprise increasing the temperature of the reaction mixture to between 180° C. and 250° C.

9. The method of claim 8, wherein the melt transesterification conditions further comprise cooling the reaction mixture of claim 8 to between 60° C. and 120° C.

10. The method of claim 2, wherein the melt transesterification catalyst is selected from the group consisting of titanium isopropoxide, a hydroxide of an alkali metal, a hydroxide of an alkaline earth metal, an alkali metal salt, an alkaline earth metal salt, a quaternary ammonium salt of boron hydride, a quaternary ammonium salt of aluminum hydride, a hydride of an alkali metal, a hydride of an alkaline earth metal, an aryloxide of an alkali metal, an aryloxide of an alkaline earth metal, an organic salt of an alkali metal, an organic salt of an alkaline earth metal, a boron compound, a silicon compound, a germanium compound, a tin compound, an organotin compound, a lead compound, an onium compound, an antimony compound, a manganese compound, a titanium compound, and a zirconium compound.

11. The method of claim 9, further comprising adding additional melt transesterification catalyst to the cooled reaction mixture to form a second reaction mixture.

12. The method of claim 11, wherein the second reaction mixture is heated to between 220° C. and 250° C.

13. The method of claim 11, wherein the melt transesterification catalyst is selected from the group consisting of titanium isopropoxide, a hydroxide of an alkali metal, a hydroxide of an alkaline earth metal, an alkali metal salt, an alkaline earth metal salt, a quaternary ammonium salt of boron hydride, a quaternary ammonium salt of aluminum hydride, a hydride of an alkali metal, a hydride of an alkaline earth metal, an aryloxide of an alkali metal, an aryloxide of an alkaline earth metal, an organic salt of an alkali metal, an organic salt of an alkaline earth metal, a boron compound, a silicon compound, a germanium compound, a tin compound, an organotin compound, a lead compound, an onium compound, an antimony compound, a manganese compound, a titanium compound, and a zirconium compound.

14. The method of claim 11, wherein the melt transesterification catalyst of the second reaction mixture is different from the melt transesterification catalyst of the first reaction mixture.

15. The method of claim 11, wherein the melt transesterification catalyst of the second reaction mixture is the same as the melt transesterification catalyst of the first reaction mixture.

* * * * *